(12) United States Patent
Kojima et al.

(10) Patent No.: US 6,534,658 B1
(45) Date of Patent: Mar. 18, 2003

(54) 1,3,4-OXADIAZOLE DERIVATIVES AND PROCESS FOR PRODUCING THE SAME

(75) Inventors: Tsutomu Kojima, Fukui (JP); Katsutoshi Hachiya, Fukui (JP); Kazuyuki Ohmoto, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/936,331

(22) PCT Filed: Mar. 10, 2000

(86) PCT No.: PCT/JP00/01464
§ 371 (c)(1),
(2), (4) Date: Dec. 19, 2001

(87) PCT Pub. No.: WO00/55145
PCT Pub. Date: Sep. 21, 2000

(30) Foreign Application Priority Data

Mar. 12, 1999 (JP) ............................................. 11-066065

(51) Int. Cl.$^7$ ...................... C07D 271/10; C07D 239/47
(52) U.S. Cl. ........................ 548/131; 546/153; 546/209; 546/269.1; 548/110; 544/319; 544/514
(58) Field of Search ................................. 548/131, 110; 546/153, 209, 269.1

(56) References Cited

U.S. PATENT DOCUMENTS 5,801,148 A       9/1998  Gyorkos et al. ............... 514/18
6,015,791 A  *    1/2000  Gyorkos et al. ............... 514/18

OTHER PUBLICATIONS

International Search Report.

\* cited by examiner

Primary Examiner—Mark Berch
Assistant Examiner—Kahsay Habte

(74) Attorney, Agent, or Firm—Sughrue Mion, PLLC

(57) ABSTRACT

Oxadiazole derivatives represented by formula (I):

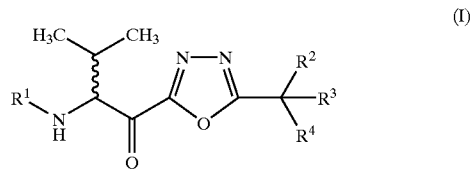

(I)

(wherein $R^1$ represents a hydrogen atom or an amino-protective group; $R^2$, $R^3$, and $R^4$ each independently represents an alkyl group, a cycloalkyl group, a phenyl group which may be substituted, or a 3,4-methylenedioxyphenyl group, or $R^3$ and $R^4$ are taken together to represent a $C_{2-6}$ alkylene group), a process of producing the same, and a process for producing oxadiazole derivatives represented by formula (II):

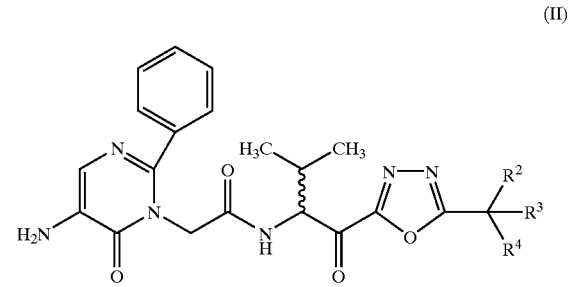

(II)

(wherein all symbols have the same meanings as described above) using the above derivative.

According to the invention, the compound represented by formula (II) is produced through fewer steps in a high yield.

9 Claims, No Drawings

1,3,4-OXADIAZOLE DERIVATIVES AND PROCESS FOR PRODUCING THE SAME

TECHNICAL FIELD

The invention relates to oxadiazole derivatives useful as intermediates for producing pharmaceuticals, a process for producing the same, and a process for producing 1,3,4-oxadiazole derivatives by using the intermediate.

More specifically, the invention relates to (1) a compound represented by formula (I):

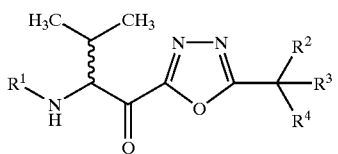

(wherein all symbols have the same meanings as described below), a non-toxic salt thereof, and a hydrate thereof;
(2) a process for producing the same, and
(3) a process for producing a compound represented by formula (II):

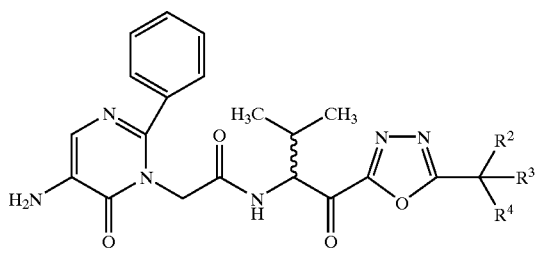

(wherein all symbols have the same meanings as described below), comprising using the same.

BACKGROUND ART

WO9824806 discloses that a compound represented by formula (W-a):

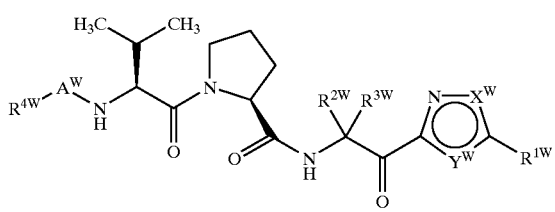

a compound represented by formula (W-b):

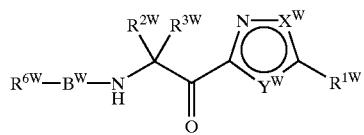

and a compound represented by formula (W-c):

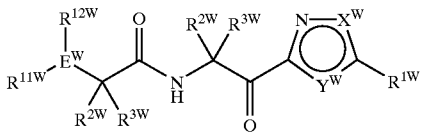

(wherein $X^w$ and $Y^w$ independently represent an oxygen atom, a sulfur atom or a nitrogen atom which may be substituted; $R^{1w}$ represents various substituents, such as an alkyl group which may be substituted, a hydroxyl group, and an amino group; $R^{2w}$ and $R^{3w}$ independently represent a hydrogen atom or various substituents, such as an alkyl group which may be substituted; $A^w$ represents a single bond, a —CO— group, an —NHCO— group, an —SO$_2$— group, or the like; $R^{4w}$ represents a hydrogen atom or various substituents, such as an alkyl group which may be substituted; $B^w$ represents an —SO$_2$— group, a —CO— group, or the like; and $R^{11w}$, $R^{12w}$, and $E^w$ are taken together to form a ring, with the proviso that these definitions are abstracts from the disclosure are useful as a serine protease (especially an elastase) inhibitor.

Upon reviewing the specification in detail, it discloses a compound represented by formula (W-c-1):

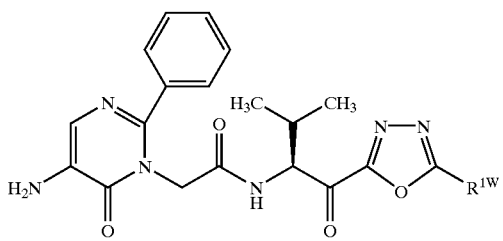

(wherein $R^{1w}$ has the same meaning as described above) among the compounds represented by general formula (W-c).

In the specification, various inhibitors are prepared using, as a key intermediate, a compound represented by formula (W-1):

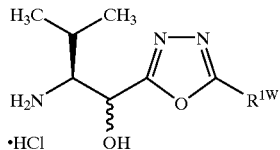

(wherein $R^{1w}$ has the same meaning as described above). According to the specification, the compound represented by formula (W-1) is produced in accordance with reaction scheme 1 or 2 shown below.

In reaction scheme 1, "Cbz" stands for a benzyloxycarbonyl group; "Py", pyridine; "TEA", triethylamine;

"DMSO", dimethyl sulfoxide; "Ac₂O", acetic anhydride; "EDC", 1-ethyl-3-[3-(dimethylamino)propyl]carbodiimide hydrochloride; "HOBt", 1-hydroxybenzotriazole; "DMF", dimethylformamide; "NMM", N-methylmorpholine; "Ts", a tosyl group; "TFA", trifluoroacetic acid; "Me", a methyl group; and "Et", an ethyl group.

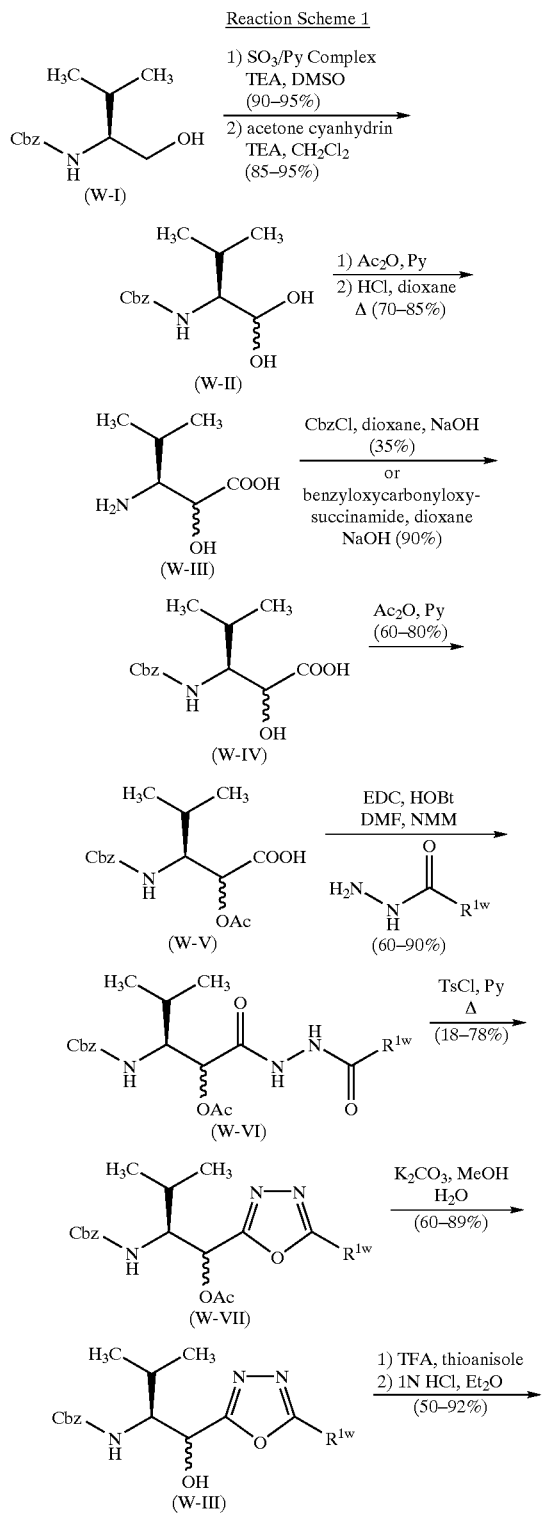

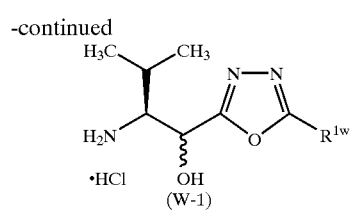

In reaction scheme 2, "Boc" stands for a t-butoxycarbonyl group; "iBu", an isobutyl group; "DIBAL", diisobutylaluminum hydride; and "n-BuLi", n-butyl lithium. Other symbols have the same meanings as described above.

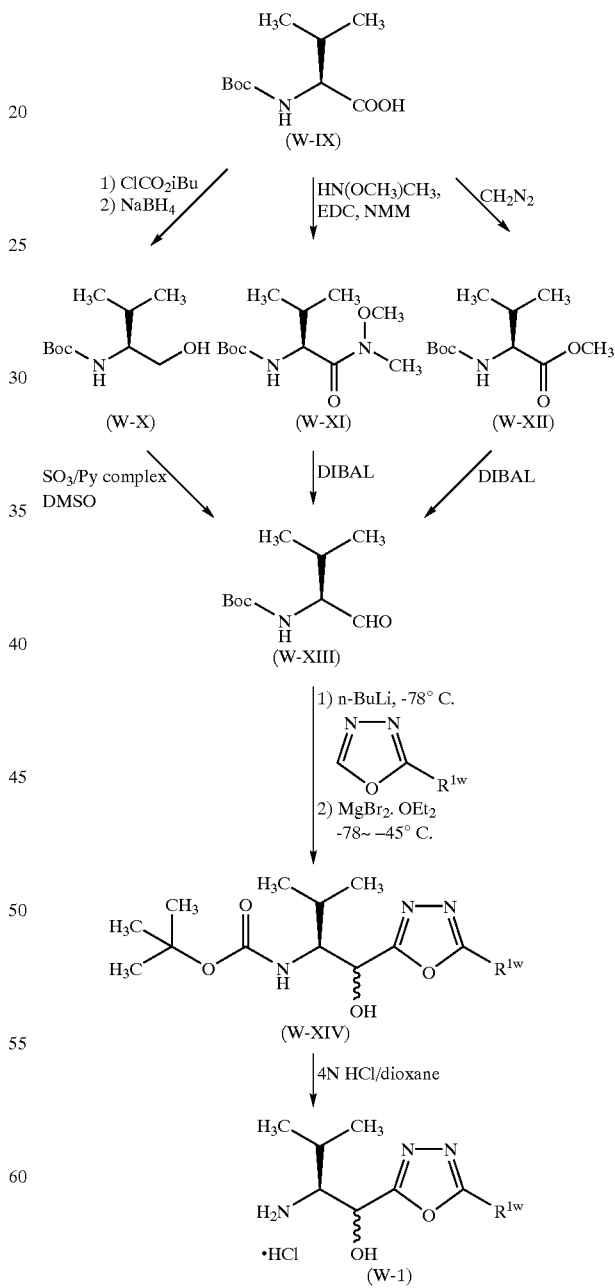

The specification also discloses that the compound represented by formula (W-c-1) among the compounds represented by formula (W-c) is produced using the compound represented by formula (W-1) in accordance with reaction scheme 3 shown below.

In reaction scheme 3, "$T^{2w}$" represents a hydrogen atom or a benzyloxycarbonylamino group, and other symbols are as defined above. The oxidation using the Dess-Martin reagent and the Swern oxidation are known oxidations.

sented by formulae (I-1) and (I-2), namely, the compounds represented by formula (I) are used as a key intermediate.

In reaction scheme 4, $R^2$, $R^3$ and $R^4$ each independently represents:
(1) a $C_{1-8}$ alkyl group,
(2) a $C_{3-7}$ cycloalkyl group,
(3) a phenyl group,

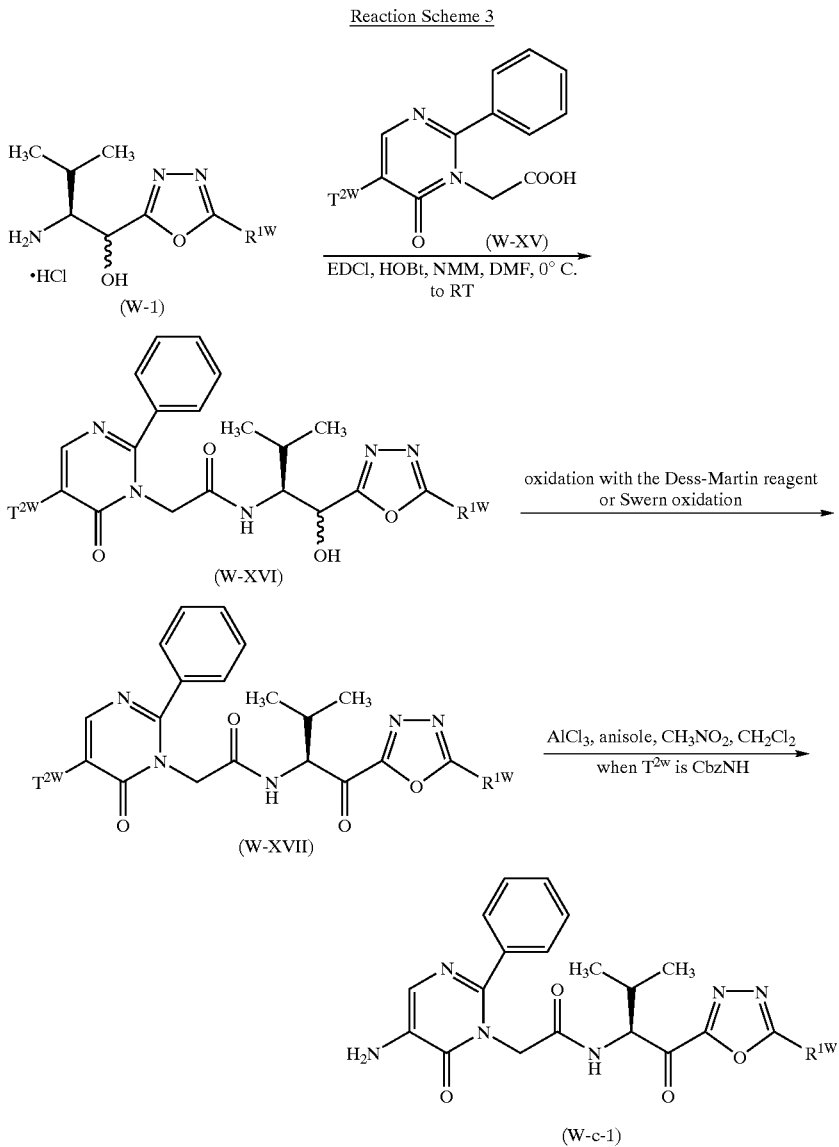

The process according to reaction scheme 1 involves a number of steps (10 steps) for producing the compound represented by formula (W-1) so that it is insufficient in efficiency.

The present inventors have conducted extensive studies seeking an efficient process for producing the compounds represented by formula (W-c-1) that are promising as pharmaceuticals. As a result, they have found a process for producing the compound represented by formula (II) shown in reaction scheme 4, in which novel compounds repre- (4) a phenyl group substituted with one to three of a $C_{1-8}$ alkyl group, a $C_{1-8}$ alkoxy group, a halogen atom, a trifluoromethyl group, and a trifluoromethoxy group, or
(5) a 3,4-methylenedioxyphenyl group; or
(6) $R^3$ and $R^4$ are taken together to represent a $C_{2-6}$ alkylene group; and $R^5$ and $R^6$ each independently represents an amino-protective group.

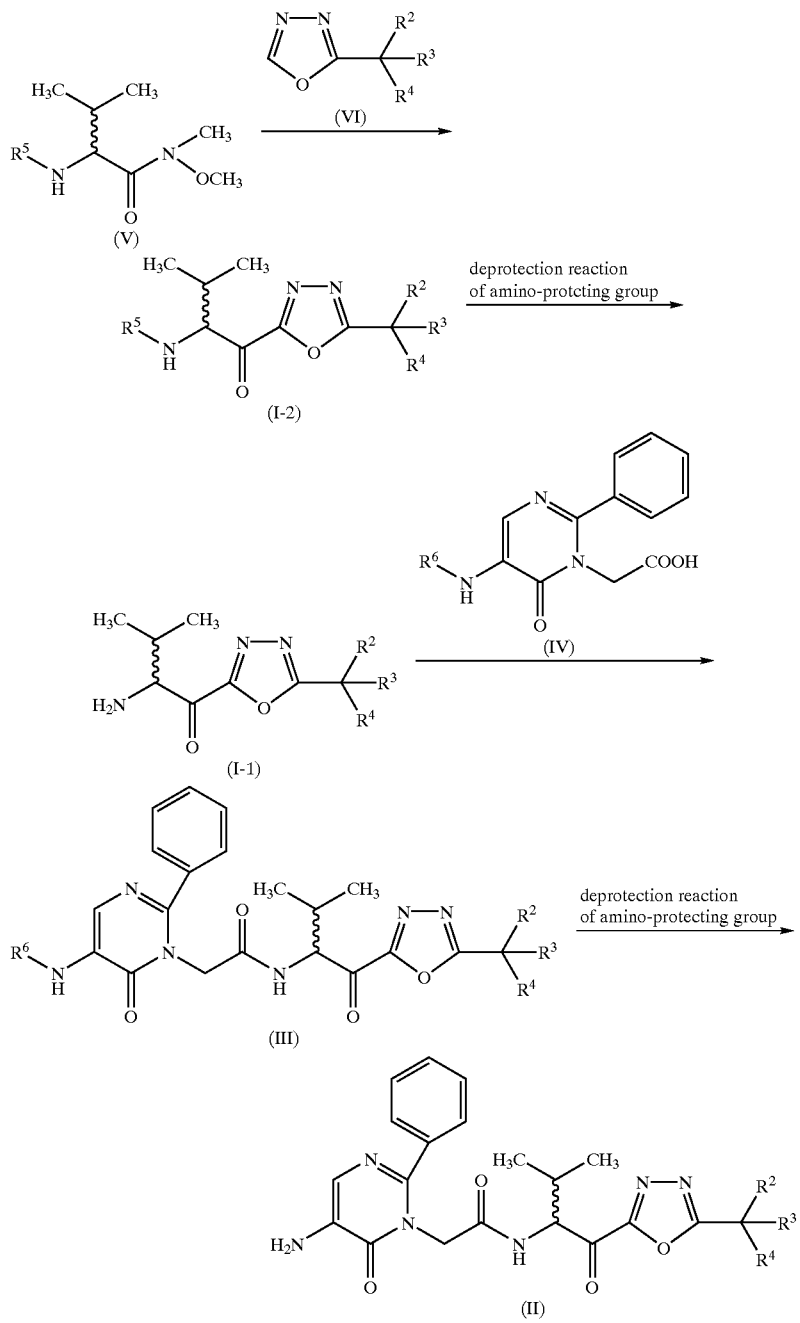

Reaction Scheme 4

The inventors have experimented the conventional processes shown in reaction schemes 2 and 3 to find that the overall synthesis yield of a compound represented by formula (II) in which $R^2$, $R^3$ and $R^4$ all represent a methyl group was 18% through six steps (see Comparative Examples described below, in which a compound represented by formula (W-XI) was used as a starting material.). In the Comparative Examples, the Swern oxidation was used as an oxidation to produce a compound represented by formula (W-XVII).

According to the process of the invention shown in reaction scheme 4, on the other hand, the overall synthesis yield of a compound represented by formula (II) wherein $R^{1w}$ is a t-butyl group was 65% through four steps (see Examples described below). In the Examples, a t-butoxycarbonyl group was used as an amino-protective group $R^5$ in the compound represented by formulae (V) and the compound represented by formula (I-2), and a benzyloxycarbonyl group was used as an amino-protective group $R^6$ in the compound represented by formula (IV) and the compound represented by formula (III).

Hence, the process of the invention makes it possible to obtain the compound represented by formula (II) through fewer steps in a higher yield. In other words, the process of the invention provides a desired compound through steps less by two in a three- to four-fold yield.

9

The present inventors have found that the compound represented by formula (II) can be prepared efficiently by the process represented by reaction scheme 4 which uses the novel compounds represented by formula (I) and thus completed the present invention.

DISCLOSURE OF THE INVENTION

The present invention relates to
1) a compound represented by general formula (I):

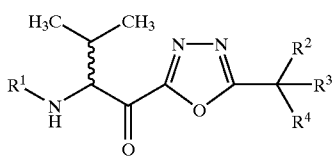

(wherein
$R^1$ represents a hydrogen atom or an amino-protective group;
$R^2$, $R^3$ and $R^4$ each independently represents
(1) a $C_{1-8}$ alkyl group,
(2) a $C_{3-7}$ cycloalkyl group,
(3) a phenyl group,
(4) a phenyl group substituted with one to three of a $C_{1-8}$ alkyl group, a $C_{1-8}$ alkoxy group, a halogen atom, a trifluoromethyl group, and a trifluoromethoxy group, or
(5) a 3,4-methylenedioxyphenyl group; or
(6) $R^3$ and $R^4$ are taken together to represent a $C_{2-6}$ alkylene group), a non-toxic salt thereof, and a hydrate thereof,
2) a process for producing the compound represented by formula (I), and
3) a process for producing a compound represented by formula (II):

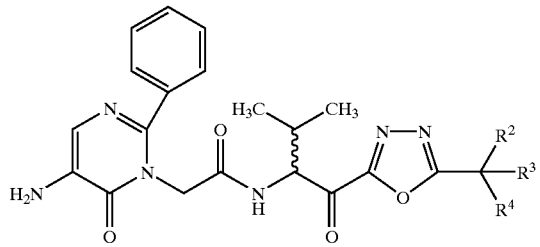

(wherein all symbols have the same meanings as described above), comprising using the compound represented by formula (I).

The term "$C_{1-8}$ alkyl group" as used herein means a methyl, ethyl, propyl, butyl, pentyl, hexyl, heptyl or octyl group or an isomer thereof.

The term "$C_{3-7}$ cycloalkyl group" as used herein means a cyclopropyl, cyclobutyl, cyclopentyl, cyclohexyl or cycloheptyl group.

The term "$C_{1-8}$ alkoxy group" as used herein means a methoxy, ethoxy, propoxy, butoxy, pentyloxy, hexyloxy, heptyloxy or octyloxy group or an isomer thereof.

The term "halogen atom" as used herein means fluorine, chlorine, bromine or iodine.

The term "$C_{2-6}$ alkylene group" as used herein means an ethylene, trimethylene, tetramethylene, pentamethylene or hexamethylene group.

10

The amino-protective group represented by $R^1$, $R^5$ or $R^6$ in the invention includes a benzyloxycarbonyl group, a t-butoxycarbonyl group, a trifluoroacetyl group and the like, but is not limited thereto, so long as it is a group which is easily and selectively removable. For example, those described in T. W. Greene, *Protective Groups in Organic Synthesis,* Wiley, New York (1991) are useful, such as methoxycarbonyl, ethoxycarbonyl, 9-fluorenylmethyloxycarbonyl, 2,2,2-trichloroethoxycarbonyl, 2-trimethylsilylethoxycarbonyl, 1,1-dimethylpropynyloxycarbonyl, 1-methyl-1-phenylethoxycarbonyl, 1-methyl-1-(4-biphenylyl)ethoxycarbonyl, 1,1-dimethyl-2-haloethoxycarbonyl, 1,1-dimethyl-2-cyanoethoxycarbonyl, t-butoxycarbonyl, cyclobutoxycarbonyl, 1-methylcyclobutoxycarbonyl, 1-adamantyloxycarbonyl, vinyloxycarbonyl, allyloxycarbonyl, cinnamyloxycarbonyl, 8-quinolyloxycarbonyl, N-hydroxypiperidinyl, benzyloxycarbonyl, p-nitrobenzyloxycarbonyl, 3,4-dimethoxy-6-nitrobenzyloxycarbonyl, 2,4-dichlorobenzyloxycarbonyl, 5-benzisoxazolylmethyloxycarbonyl, 9-anthrylmethyloxycarbonyl, diphenylmethyloxycarbonyl, isonicotinyloxycarbonyl, benzylthiocarbonyl, N'-phenylaminothiocarbonyl, formyl, acetyl, chloroacetyl, trichloroacetyl, trifluoroacetyl, benzoyl, allyl, phenylacetyl, methoxymethyl, benzyloxymethyl, 2,4-dinitrophenyl, 2-nitrobenzyl, 2-(trimethylsilyl)ethoxymethyl, benzyl, triphenylmethyl, p-toluenesulfonyl, benzenesulfonyl and benzylsulfonyl.

The amino-protective group represented by $R^1$ and $R^5$ is preferably a t-butoxycarbonyl group or a benzyloxycarbonyl group, and more preferably a t-butoxycarbonyl group.

The amino-protective group represented by $R^6$ is preferably a benzyloxycarbonyl group.

In the present invention, the group represented by

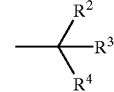

is preferably a group in which $R^2$, $R^3$ and $R^4$ each represents a $C_{1-8}$ alkyl group; a group in which $R^2$ represents a phenyl group, and $R^3$ and $R^4$ each represents a $C_{1-8}$ alkyl group; a group in which $R^2$ represents a 3,4-methylenedioxyphenyl group, and $R^3$ and $R^4$ each represents a $C_{1-8}$ alkyl group; and a group in which $R^2$ represents a $C_{1-8}$ alkyl group, and $R^3$ and $R^4$ are taken together to represent a $C_{2-6}$ alkylene group;
more preferably a group in which $R^2$, $R^3$, and $R^4$ each represents a $C_{1-4}$ alkyl group; a group in which $R^2$ represents a phenyl group, and $R^3$ and $R^4$ each represents a $C_{1-4}$ alkyl group; a group in which $R^2$ represents a 3,4-methylenedioxyphenyl group, and $R^3$ and $R^4$ each represents a $C_{1-4}$ alkyl group;
and a group in which $R^2$ represents a $C_{1-4}$ alkyl group, and $R^3$ and $R^4$ are taken together to represent a $C_{2-5}$ alkylene group, and
most preferably, the group

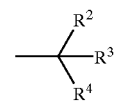

represents an α,α-dimethyl-3,4-methylenedioxybenzyl group, a t-butyl group, an α,α-dimethylbenzyl group or a 1-methylcyclopropyl group.

In the invention, as is apparent to one skilled in the art, the mark

shows that the bond is in front of paper (at the β-position) unless otherwise indicated; the mark

indicates that the bond is on the other side of paper (at the α-position) unless otherwise indicated; the mark

shows that the compound has the bond at the β-position or the α-position or the compound is a mixture of these compounds; and the mark

indicates that the compound is a mixture of a compound having the bond at the β-position and a compound having the bond at the α-position.

In the invention, all conceivable isomers are included in the scope thereof unless otherwise indicated. For example, an alkyl group, an alkoxy group and an alkylene group include straight-chain groups and branched groups. Isomers caused by the presence of an asymmetric carbon (e.g., R or S-forms, α- or β-forms, enantiomers, and diastereomers) and optically active compounds having optical rotation (i.e., D-, L-, d- or l-forms) are all included within the scope of the invention.

PROCESS OF PRODUCING THE COMPOUND OF INVENTION

The compound represented by formula (I) can be produced by processes (1) and (2) described below, the processes according to Examples described below, or known processes.

(1) Among the compounds represented by formula (I), a compound in which $R^1$ represents an amino-protective group, i.e., a compound represented by formula (I-2):

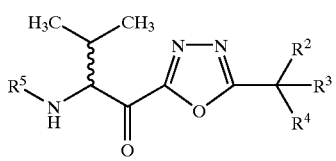

(I-2)

(wherein all symbols have the same meanings as described above) is prepared by reacting a compound represented by formula (V):

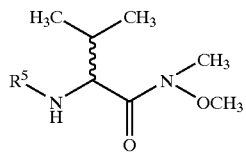

(V)

(wherein $R^5$ has the same meaning as described above) and a compound represented by formula (VI):

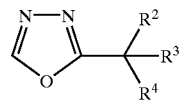

(VI)

(wherein all symbols have the same meanings as described above).

The reaction between the compound represented by formula (V) and the compound represented by formula (VI) is carried out in an inert organic solvent (e.g., chloroform, methylene chloride, diethyl ether, tetrahydrofuran, toluene, dimethylformamide, or the like) in the presence of a base (e.g., lithium diisopropylamide (LDA), or the like) and a tertiary amine (e.g., tetramethylethylenediamine, or the like) at −78 to 0° C.

(2) Among the compounds represented by formula (I), a compound in which $R^1$ is a hydrogen atom, i.e., a compound represented by formula (I-1):

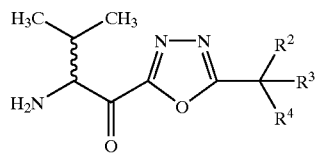

(I-1)

(wherein all symbols have the same meanings as described above) is prepared by subjecting the compound represented by formula (I-2) to a deprotection reaction of the amino-protecting group.

The deprotection reaction for the amino-protecting group includes, for example,
1) a deprotection reaction under alkaline conditions,
2) a deprotection reaction under acidic conditions, and
3) a deprotection reaction by hydrolysis.

More specifically,
1) the deprotection reaction under alkaline conditions is carried out, for example, at 0° C. to 40° C. in an organic solvent (e.g., methanol, tetrahydrofuran, dioxane, dimethylformamide, or the like) using an alkali metal hydroxide (e.g., sodium hydroxide, potassium hydroxide, lithium hydroxide, or the like), an alkaline earth metal hydroxide (e.g., barium hydroxide, calcium hydroxide, or the like), an organic amine (e.g., triethylamine, N-methylmorpholine, diisopropylethylamine, piperidine, or the like) or a quaternary ammonium salt (e.g., tetrabutylammonium fluoride, or the like) an aqueous solution thereof or a mixture thereof.
2) The deprotection reaction under acidic conditions is carried out, for example, at 0° C. to 100° C. in an organic solvent (e.g., methylene chloride, chloroform, dioxane, ethyl acetate, anisole, or the like) or without a solvent using an organic acid (e.g., acetic acid, trifluoroacetic acid, methanesulfonic acid, trimethylsilyl iodide, or the like) or an inorganic acid (e.g., hydrochloric acid, sulfuric acid, or the like), or a mixture thereof (e.g., hydrogen bromide/acetic acid, or the like).

3) The deprotection reaction by hydrolysis is carried out, for example, in an inert solvent (e.g., ethers (tetrahydrofuran, dioxane, dimethoxyethane, diethyl ether, etc.), alcohols (methanol, ethanol, etc.), benzene solvents (benzene, toluene, etc.), ketones (acetone, methyl ethyl ketone, etc.), nitriles (acetonitrile, etc.), amides (dimethylformamide, etc.), water, ethyl acetate, acetic acid, or mixed solvent of two or more thereof) in the presence of a hydrogenation catalyst (e.g., palladium-carbon, palladium black, palladium, palladium hydroxide, platinum dioxide, nickel, Raney nickel, ruthenium chloride, or the like) and in the presence or absence of an inorganic acid (e.g., hydrochloric acid, sulfuric acid, hypochloric acid, boric acid, tetrafluoroboric acid, or the like) or an organic acid (e.g., acetic acid, p-toluenesulfonic acid, oxalic acid, trifluoroacetic acid, formic acid, or the like) in a hydrogen atmosphere either under normal pressure or under pressure or in the presence of ammonium formate at a 0° C. to 200° C. In using an acid, the acid may be used in the form of its salt.

As is easily understood by one skilled in the art, the desired compound of the invention can be easily obtained by a proper choice of these reactions.

The deprotection reaction of the compound represented by formula (I-2) is preferably carried out by the reaction under acidic conditions or the reaction by hydrolysis. The reaction under acidic conditions is more preferred.

The compound represented by formula (I-1) is allowed to react with the compound represented by formula (IV):

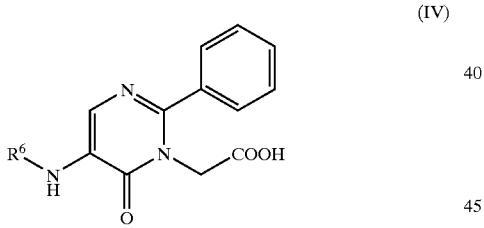

(IV)

(wherein $R^6$ has the same meaning as described above) to produce the compound represented by formula (III):

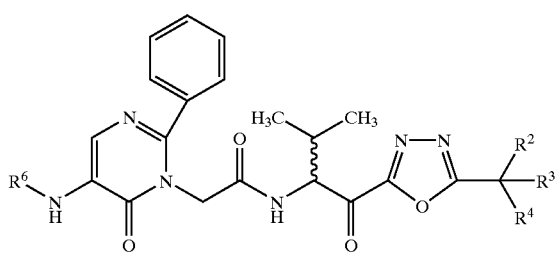

(III)

(wherein all symbols have the same meanings as described above). The reaction for producing the compound represented by formula (III) is an amidation.

The amidation is known in the art. It includes, for example, 1) a process using an acid halide,
2) a process using a mixed acid anhydride, and
3) a process using a condensing agent.

More specifically, 1) the process using an acid halide is carried out by, for example, reacting the compound represented by formula (IV) with an acid halide (e.g., oxalyl chloride thionyl chloride, or the like) in an inert organic solvent (e.g., chloroform, methylene chloride, diethyl ether, tetrahydrofuran, or the like) or without a solvent at −20° C. to a refluxing temperature and reacting the resulting acid halide with the compound represented by formula (I-1) in an inert organic solvent (e.g., chloroform, methylene chloride, diethyl ether, tetrahydrofuran, or the like) in the presence of a tertiary amine (e.g., pyridine, triethylamine, dimethylaniline, dimethylaminopyridine, or the like) at −20° C. to 40° C.

2) The process using a mixed acid anhydride is carried out by, for example, reacting the compound represented by formula (IV) with an acid halide (e.g., pivaloyl chloride, tosyl chloride, mesyl chloride, or the like) or an acid derivative (e.g., ethyl chloroformate (ethyl chlorocarbonate), isobutyl chloroformate (isobutyl chlorocarbonate), or the like) in an inert organic solvent (e.g., chloroform, methylene chloride, diethyl ether, tetrahydrofuran, or the like) or without a solvent in the presence of a tertiary amine (e.g., pyridine, triethylamine, dimethylaniline, dimethylaminopyridine, N-methylmorpholine, or the like) at −20° C. to 40° C. and reacting the resulting mixed acid anhydride with the compound represented by formula (I-1) in an inert organic solvent (e.g., chloroform, methylene chloride, diethyl ether, tetrahydrofuran, or the like) at −20° C. to 40° C.

3) The process using a condensing agent is conducted by, for example, reacting the compound represented by formula (IV) with the compound represented by formula (I-1) in an organic solvent (e.g., chloroform, methylene chloride, dimethylformamide, diethyl ether, tetrahydrofuran, or the like) or without a solvent in the presence or absence of a tertiary amine (e.g., pyridine, triethylamine, dimethylaniline, dimethylaminopyridine, or the like) using a condensing agent (e.g., 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, or the like) and with or without 1-hydroxybenztriazole (HOBt) at 0° C. to 40° C.

The reactions 1), 2) and 3) are preferably carried out in an atmosphere of an inert gas (e.g., argon, nitrogen, or the like) under anhydrous conditions.

The amidation between the compound represented by formula (I-1) and the compound represented by formula (IV) is preferably carried out by the process using a mixed acid anhydride.

The reaction for converting the compound represented by formula (III) into the compound represented by formula (II) can be carried out by the above deprotection reaction of the amino-protecting group.

The deprotection reaction of the amino-protecting group for converting the compound represented by formula (III) into the compound represented by formula (II) is preferably carried out by hydrolysis.

The compound represented by formula (V) and the compound represented by formula (VI) are produced by the process described in WO9824806 or Examples described below.

The compound represented by formula (IV) is produced by the process described in EP 528633 (JP-A-5-286946).

The other starting materials and reagents used in the present invention are known per se or can be prepared by known processes.

As is easily understood by one skilled in the art, the compounds represented by formulas (I-2), (I-1), (III) and (II) in their optically active form can be easily produced using an optically active compound as the compound represented by formula (V).

For example, among the compounds represented by formula (V), t-butyl N-((1R)-1-(N'-methyl-N'-methoxyaminocarbonyl)-2-methylpropyl)carbamate (CAS Registry No. 190260-92-5), t-butyl N-((1S)-1-(N'-methyl-N'-methoxyaminocarbonyl)-2-methylpropyl)carbamate (CAS Registry No. 160711-20-6), benzyl N-((1S)-1-(N'-methyl-N'-methoxyaminocarbonyl)-2-methylpropyl)carbamate (CAS Registry No. 114744-84-2), and the like are known. Use of these optically active compounds easily provides, for example, N-((1R)-1-(2-t-butyl-1,3,4-oxadiazol-5-ylcarbonyl)-2-methylpropyl)-2-(5-benzyloxycarbonylamino-6-oxo-2-phenyl-1,6-dihydropyrimidin-1-yl)acetamide, N-((1S)-1-(2-t-butyl-1,3,4-oxadiazol-5-ylcarbonyl)-2-methylpropyl)-2-(5-benzyloxycarbonylamino-6-oxo-2-phenyl-1,6-dihydropyrimidin-1-yl)acetamide, and the like among the compounds represented by formula (III); and N-(1R)-1-(2-t-butyl-1,3,4-oxadiazol-5-ylcarbonyl)-2-methylpropyl)-2-(5-amino-6-oxo-2-phenyl-1,6-dihydropyrimidin-1-yl)acetamide, N-((1S)-1-(2-t-butyl-1,3,4-oxadiazol-5-ylcarbonyl)-2-methylpropyl)-2-(5-amino-6-oxo-2-phenyl-1,6-dihydropyrimidin-1-yl)acetamide, and the like among the compounds represented by formula (II).

The product of each reaction in the invention is purified through common purification means, for example, distillation under normal pressure or reduced pressure, high performance liquid chromatography using silica gel or magnesium silicate, thin layer chromatography, column chromatography, washing, recrystallization, and the like. The purification may be carried out at each reaction or after completion of several reactions.

The compound represented by general formula (I) can be converted into a salt by a known method. The salt is preferably non-toxic and water-soluble. Examples of suitable salts include salts with alkali metals (e.g., potassium, sodium, and the like), salts with alkaline earth metals (e.g., calcium, magnesium, and the like), ammonium salts, and pharmaceutically acceptable salts with organic amines (e.g., tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, and the like).

The compound represented by formula (I) according to the present invention can be converted into an acid addition salt by a known process. The acid addition salt is preferably non-toxic and water-soluble. Examples of suitable acid addition salts include inorganic acid salts, such as hydrochlorides, hydrobromides, sulfates, phosphates, nitrates, and the like; and organic acid salts, such as acetates, trifluoroacetates, lactates, tartrates, oxalates, fumarates, maleates, citrates, benzoates, methanesulfonates, ethanesulfonates, benzenesulfonates, toluenesulfonates, isethionates, glucuronates, gluconates, and the like.

The compound represented by formula (I) according to the invention or a non-toxic salt thereof can be converted into a hydrate thereof by a known method.

Industrial Applicability

The process of the invention provides the compound represented by formula (II) through a fewer steps using the novel intermediate represented by formula (I) and is therefore useful as an efficient industrial process of production.

BEST MODE FOR CARRYING OUT THE INVENTION

The present invention will now be illustrated in greater detail by way of Reference Examples, Examples, and Comparative Examples, but the invention is not limited thereto.

Solvents in parentheses shown in the part of chromatographic separation and TLC are eluents or developing solvents used, and ratios are by volume.

Solvents in parentheses shown in the part of NMR are solvents used for the measurement.

Reference Example 1

Synthesis of t-butyl N-(1-(N'-methyl-N'-methoxyaminocarbonyl)-2-methylpropyl)carbamate

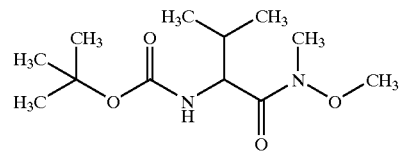

N,O-Dimethylhydroxylamine hydrochloride (3.37 kg) and 1-ethyl-3-[3-(dimethylamino)propyl]carbodiimide (5.73 kg) were dissolved in pyridine (19 liters (L)) at room temperature in a nitrogen atmosphere, and 2-t-butoxycarbonylamino-3-methylbutanoic acid (5.00 kg) was added thereto at 5° C. or lower, followed by stirring at 20–30° C. for 2 hours. Ice-water (23.8 L) and toluene (15.8 L) were added to the reaction mixture, and the resulting layers were separated. The aqueous layer was extracted with a mixed solvent (toluene:ethyl acetate=1:1, 15.8 L). The organic layers were combined and washed with 1N hydrochloric acid (40 L, twice). Ethyl acetate (7.9 L) was added to the organic layer, and the mixture was washed with a saturated aqueous solution of sodium hydrogencarbonate (16 L, twice), water (30 L, twice), and saturated saline (16 L, twice) successively, followed by concentration. The residue was dissolved in methanol (12 L) at 40° C., and water (30 L) was added thereto to precipitate a solid, followed by stirring at 25° C. for 2 hours and then at 5° C. or lower for 2 at least hours. The precipitated solid was filtrated and washed with water (5 L). The solid was dried in vacuo at 30° C. for at least 15 hours to obtain the title compound (5.16 kg; yield: 86%) having the following physical properties.

TLC: Rf 0.49 (hexane:ethyl acetate=2:1)

NMR (CDCl$_3$): δ5.13 (brd, 1H), 4.57 (brt, 1H), 3.77 (s, 3H), 3.22 (s, 3H), 1.97 (m, 1H), 1.44 (s, 9H), 0.96 (d, J=6.8 Hz, 3H), 0.91 (d, J=6.8 Hz, 3H).

Reference Example 2
Synthesis of Pivaloylhydrazine

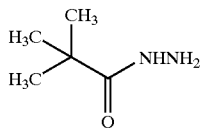

Methyl pivalate (1040 ml) and hydrazine monohydrate (760 ml) were heated under reflux for 14.5 hours in an argon stream. The reaction mixture was cooled to room temperature and concentrated. The residue was cooled with ice, and the precipitated crystals were collected by filtration. The filtered material was washed with hexane (250 ml, twice; and 300 ml, once) to obtain the title compound. Furthermore, the mother liquid (510 g) was cooled with ice, and the precipitated crystals were collected by filtration. The filtered material was washed with hexane (100 ml, twice; and 200 ml, once) to obtain the title compound having the following physical properties (total yield: 571.8 g, 63%).

TLC: Rf 0.59 (chloroform:methanol=10:1)

NMR (CDCl$_3$): δ7.06 (brs, 1H), 3.87 (brs, 2H), 1.21 (s, 9H)

Reference Exmaple 3

Synthesis of 2-t-butyl-1,3,4-oxadiazole

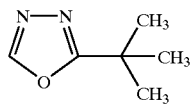

A mixture of the compound produced in Reference Example 2 (570 g), methyl orthoformate (805 ml) and p-toluenesulfonic acid monohydrate (14.0 g) was heated under stirring for 9 hours while distilling off produced methanol. The reaction mixture was cooled to room temperature and distilled under reduced pressure to obtain a compound of the invention (538.4 g; 86%) having the following physical properties.

TLC: Rf 0.68 (chloroform:methanol=10:1)

NMR (CDCl$_3$): δ8.33 (s, 1H), 1.45 (s, 9H)

Reference Exmalpe 4

Synthesis of N-hydroxy-1-(2,2-dimethoxyethyl)-6-oxo-2-phenyl-1,6-dihydropyrimidin-5-ylcarboxamide

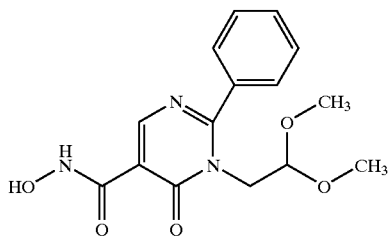

Triethylamine (49.4 ml) was added to a solution of 1-(2,2-dimethoxyethyl)-6-oxo-2-phenyl-1,6-dihydropyrimidin-5-ylcarboxylic acid (97.3 g) in tetrahydrofuran (800 ml) in an ice bath in an argon atmosphere, and isobutyl chlorocarbonate (45.6 ml) was added dropwise thereto at 5° C. or lower, followed by stirring at the same temperature for 1 hour. To the reaction mixture was added a 50% hydroxylamine aqueous solution (422 ml), followed by stirring for 20 minutes. The reaction mixture was separated to layers. The aqueous layer was extracted with ethyl acetate (200 ml). The organic layers were combined, washed with saturated saline (200 ml), and concentrated. To the residue was added toluene (200 ml), followed by concentration. The resulting crude crystals were washed with isopropyl ether (1000 ml) by heating under reflux for 10 minutes, cooled to room temperature, and crystals were collected by filtration. The collected crystals were dried in vacuo at room temperature overnight to obtain the title compound (93.3 g; yield: 91%) having the following physical properties.

TLC: RF 0.5 (ethyl acetate);

NMR (CDCl$_3$): δ8.95 (s, 1H), 7.62–7.45 (m, 5H), 4.76 (t, J=5.8 Hz, 1H), 4.21 (2H, d, J=5.8 Hz), 3.30 (6H, s).

Reference Example 5

Synthesis of N-acetyloxy-1-(2,2-dimethoxyethyl)-6-oxo-2-phenyl-1,6-dihydropyrimidin-5-ylcarboxamide

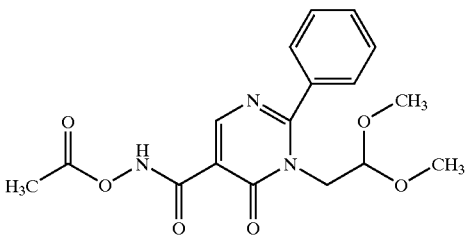

Pyridine (5.66 ml) was added to a suspension of the compound produced in Reference Example 4 (15.95 g) in tetrahydrofuran (50 ml) at room temperature in an argon atmosphere, and acetic anhydride (5.19 ml) was added dropwise thereto, followed by stirring for 20 minutes. Ethyl acetate (150 ml) and 1N hydrochloric acid (84 ml) were added to the reaction mixture, and the resulting layers were separated. The organic layer was washed with an aqueous sodium chloride solution (saturated saline (50 ml) and water (50 ml)) and a mixed solution (saturated saline (50 ml) and a saturated aqueous solution of sodium hydrogencarbonate (50 ml)) successively, followed by concentration to obtain the title compound (16.9 g; crude product) having the following physical properties.

TLC: Rf 0.44 (toluene:acetone=4:1)

NMR (CDCl$_3$): δ8.99 (s, 1H), 7.62–7.45 (m, 5H), 4.79 (t, J=5.4 Hz, 1H), 4.22 (d, J=5.4 Hz, 2H), 3.30 (s, 6H), 2.30 (s, 3H).

Reference Example 6

Synthesis of 5-amino-1-(2,2-dimethoxyethyl)-6-oxo-2-phenyl-1,6-dihydropyrimidine

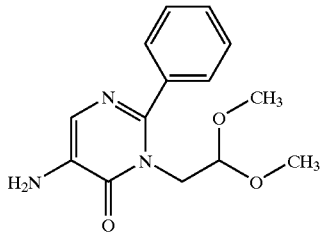

A suspension of the compound produced in Reference Example 5 (16.9 g) in tetrahydrofuran (200 ml) was heated to obtain a solution. Water (18 ml) was added thereto at 40° C., and 1,8-diazabicyclo[5.4.0]-7-undecene (9.35 ml) was added thereto at 50° C., followed by heating under reflux for 1 hour. After cooling the reaction mixture to room temperature, toluene (100 ml) and a saturated aqueous solution of ammonium chloride (100 ml) were added thereto, and the resulting layers were separated. The organic layer was washed with a saturated aqueous ammonium chloride solution and saturated saline (100 ml) successively and concentrated to obtain the title compound (15.7 g; crude product) having the following physical properties.

TLC: Rf 0.26 (toluene:acetone=4:1)

NMR (CDCl$_3$): δ7.55–7.38 (m, 6H), 4.77 (t, J=5.6 Hz, 1H), 4.14 (d, J=5.6 Hz, 2H), 4.02 (brs, 2H), 3.27 (s, 6H)

Reference Example 7

Synthesis of 5-benzyloxycarbonylamino-1-(2,2-dimethoxyethyl)-6-oxo-2-phenyl-1,6-dihydropyrimidine

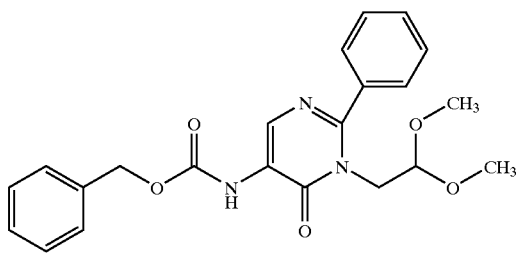

A mixture of the compound produced in Reference Example 6 (15.7 g), tetrahydrofuran (75 ml), water (75 ml), and sodium hydrogencarbonate (5.88 g) was cooled with ice, and benzyloxycarbonyl chloride (8.56 ml) was added dropwise thereto at 5° C. or lower, followed by stirring at 5° C. overnight. Ethyl acetate (100 ml) was added to the reaction mixture, and the resulting layers were separated. The organic layer was washed with saturated saline (100 ml), followed by concentration to obtain the title compound (22.0 g; crude product) having the following physical properties.

TLC: Rf 0.67 (toluene:acetone=4:1)

NMR (CDCl$_3$): δ8.73 (brs, 1H), 7.60–7.30 (m, 10H), 5.24 (s, 2H), 4.71 (t, J=5.5 Hz, 1H), 4.15 (d, J=5.5 Hz, 2H), 3.26 (s, 6H)

Reference Example 8

Synthesis of 5-benzyloxycarbonylamino-1-formylmethyl-6-oxo-2-phenyl-1,6-dihydropyrimidine

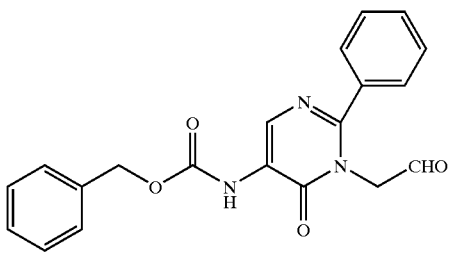

A mixture of the compound produced in Reference Example 7 (22.0 g), 1N hydrochloric acid (10 ml), and acetic acid (30 ml) was heated to 70–77° C., followed by stirring for 2 hours. The reaction mixture was cooled to room temperature, water (75 ml) and a mixed solvent (toluene:ethyl acetate=4:1, 60 ml) were added thereto, and the resulting layers were separated. The aqueous layer was extracted with a mixed solvent (toluene:ethyl acetate=4:1, two 30 ml portions). The organic layers were combined and washed with water (50 ml), a saturated aqueous solution of sodium hydrogencarbonate (50 ml), and saturated saline (50 ml) successively, and dried over anhydrous magnesium sulfate, followed by concentration to obtain the title compound (16.8 g; crude product) having the following physical properties.

TLC: Rf 0.36 (hexane:ethyl acetate=1:1)

NMR (CDCl$_3$): δ9.59 (s, 1H), 8.79 (brs, 1H), 7.60–7.10 (m, 10H), 5.24 (s, 2H), 4.77 (s, 2H)

Reference Example 9

Synthesis of 5-benzyloxycarbonylamino-6-oxo-2-phenyl-1,6-dihydropyrimidin-1-ylmethylcarboxylic acid

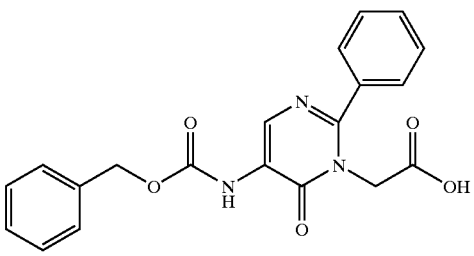

An aqueous solution (20 ml) of sodium dihydrogenphosphate (7.20 g) was added to a solution of the compound produced in Reference Example 8 (16.8 g) in a mixed solvent (t-butanol:water=4:1, 100 ml), followed by cooling with ice. To the reaction mixture was added 2-methyl-2-butene (23.8 ml), and an aqueous solution (32 ml) of sodium chlorite (19.78 g) was added dropwise thereto, followed by stirring at room temperature for 3 hours. Ethyl acetate (30 ml) was added to the reaction mixture, and the resulting layers were separated. To the organic layer were added a saturated aqueous sodium chloride solution (60 ml) and ethyl acetate (30 ml), and the resulting layers were separated. The organic layer was washed with a 10% aqueous solution of sodium hydrogensulfite (60 ml). The aqueous layer was extracted with ethyl acetate (50 ml). The organic layers were combined and washed with 1 N hydrochloric acid (60 ml) and saturated saline (60 ml) successively, and dried over anhydrous magnesium sulfate, followed by concentration. Ethyl acetate (50 ml) was added to the residue, followed by concentration. Ethyl acetate (50 ml) was further added to the residue, followed by concentration. To the resulting crude crystals was added ethyl acetate (35 ml), followed by heating under reflux for 15 minutes. Isopropyl ether (17.5 ml) was added, followed by heating under reflux for further 15 minutes. The solution was cooled to room temperature, followed by stirring at 5° C. overnight. The precipitated crystals were collected by filtration, and washed with isopropyl ether (50 ml). The crystals were dried in vacuo to obtain the compound of the invention (11.99 g; yield: 63%) having the following physical properties.

TLC: Rf 0.55 (chloroform:methanol:acetic acid=18:1:1)

NMR (CD$_3$OD): δ8.65 (s, 1H), 7.60–7.25 (m, 10H), 5.23 (s, 2H), 4.60 (s, 2H)

EXAMPLE 1

Synthesis of t-butyl N-(1-(2-t-butyl-1,3,4-oxadiazol-5-ylcarbonyl)-2-methylpropyl)carbamate

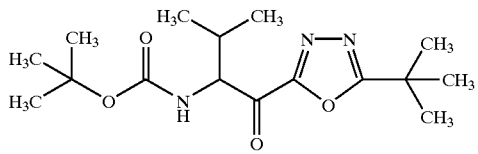

A 2.0 M solution of lithium diiospropylamide (19.65 kg) was added dropwise to a solution of the compound produced in Reference Example 1 (2.52 kg), the compound produced in Reference Example 3 (6.10 kg), and tetramethylethylenediamine (5.62 kg) in tetrahydrofuran (25.2 L) at −65° C. or less in an argon stream, followed by stirring at −25° C. to −20° C. for 3 to 5 hours. The reaction mixture was poured into a cool 10% aqueous citric acid solution (93 L) and extracted with ethyl acetate. To the organic layer was added 1N hydrochloric acid (96.8 L), followed by stirring for 1 hour, and the resulting layers were separated. The organic layer was washed with a 5% aqueous potassium carbonate solution (50.4 L), water (25.2 L, twice), and saturated saline (8.4 L) successively, and dried over anhydrous magnesium sulfate. The anhydrous magnesium sulfate was separated by filtration and washed with tetrahydrofuran (2.8 L). The organic layer was concentrated to obtain the compound of the invention (3.69 kg, crude product) having the following physical properties.

TLC: Rf 0.70 (hexane:ethyl acetate=2:1)

NMR (CDCl$_3$): δ5.30–5.05 (m, 2H), 2.46 (m, 1H), 1.48 (s, 9H), 1.43 (s, 9H), 1.09 (d, J=6.9 Hz, 3H), 0.88 (d, J=6.9 Hz, 3H).

EXAMPLE 1(1)

Synthesis of t-butyl N-((2S)-1-(2-α,α-dimethylbenzyl)-1,3,4-oxadiazol-5-ylcarbonyl)-2-methylpropyl)carbamate

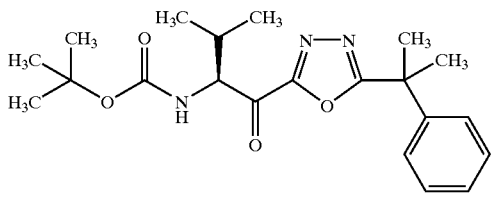

The compound of the invention having the following physical properties was obtained in the same manner as in Example 1, except for replacing the compound produced in Reference Example 3 with a corresponding oxadiazole derivative and replacing the compound produced in Reference Example 1 with t-butyl N-((2S)-1-(N'-methyl-N'-methoxyaminocarbonyl)-2-methylpropyl)carbamate.

TLC: Rf 0.50 (ethyl acetate:n-hexane=1:2)

NMR (CDCl$_3$): δ7.32 (m, 5H), 5.16 (m, 2H), 2.45 (m, 1H), 1.89 (s, 6H), 1.43 (s, 9H), 1.07 (d, 3H, J=6.8 Hz), 0.86 (d, 3H, J=7.2 Hz)

EXAMPLE 2

Synthesis of 1-(2-t-butyl-1,3,4-oxadiazol-5-ylcarbonyl)-2-methylpropylamine Hydrochloride

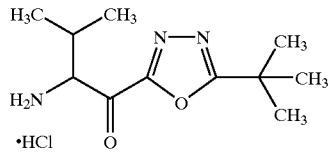

A solution of the compound produced in Example 1 (3.15 kg) in ethyl acetate (4.3 L) was added dropwise to a 4N hydrogen chloride-ethyl acetate solution (9.7 L) at 10–20° C. in a nitrogen stream, followed by stirring for 1.5–2 hours. A 4N hydrogen chloride-ethyl acetate solution (4.8 L) was added to the reaction mixture at 10–20° C., followed by stirring for 1 hour. The reaction mixture was concentrated, ethyl acetate (8.8 L) was added thereto, followed by concentration. Ethyl acetate (8.8 L) was again added to the concentrate, followed by concentration. t-Butyl methyl ether (29.0 L) was added to the concentrate, followed by stirring at 5° C. or lower for at least 2 hours. The precipitated solid was collected by filtration. The filtered solid was washed with a mixed solvent (t-butyl methyl ether (3.84 L) and ethyl acetate (0.96 L)) and dried in vacuo at 30° C. for at least 15 hours to obtain the compound of the invention (2.16 kg; yield through the two steps: 86%) having the following physical properties.

TLC: Rf 0.90 (chloroform:methanol=10:1)

NMR (CD$_3$OD): δ5.05 (d, J=3.8 Hz, 1H), 2.85 (m, 1H), 1.48 (s, 9H), 1.35 (d, J=6.9 Hz, 3H), 1.10 (d, J=6.9 Hz, 3H)

EXAMPLE 2(1)

Synthesis of (2S)-1-(2-(α,α-dimethylbenzyl)-1,3,4-oxadiazol-5-ylcarbonyl)-2-methylpropylamine Hydrochloride

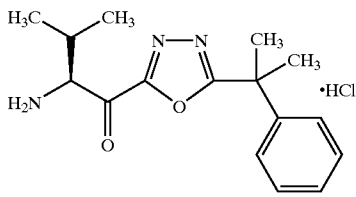

The compound of the invention having the following physical properties was obtained in the same manner as in Example 2, except for replacing the compound produced in Example 1 with the compound produced in Example 1(1).

TLC: Rf 0.50 (chloroform:methanol=10:1)

NMR (CDCl$_3$): δ9.05 (brs, 2H), 7.28 (m, 5H), 4.96 (m, 1H), 2.79 (m, 1H), 1.87 (s, 6H), 1.29 (d, J=6.8 Hz, 3H), 1.02 (d, J=7.2 Hz, 3H)

EXAMPLE 3

Synthesis of N-((1RS)-1-(2-t-butyl-1,3,4-oxadiazol-5-ylcarbonyl)-2-methylpropyl)-2-(5-benzyloxycarbonylamino-6-oxo-2-phenyl-1,6-dihydropyrimidin-1-yl)acetamide

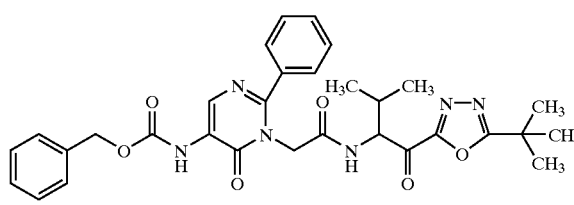

N-Methylmorpholine (634 g) was added to a solution of the compound produced in Reference Example 9 (2.38 kg) in tetrahydrofuran (12.9 L) at −5° C. or lower in an argon stream, ethyl chlorocarbonate (680 g) was added dropwise thereto at −2° C. or lower, and the reaction mixture was stirred at −5° C. or lower for 30 minutes. The compound produced in Example 2 (1.64 kg) was added to the reaction mixture at −5° C. or lower, followed by stirring for 30 minutes. To the reaction mixture was added N-methylmorpholine (634 g) at −5° C. or lower, followed by stirring for 30 minutes. t-Butyl methyl ether (24.8 L) and 1N hydrochloric acid (12.9 L) were added to the reaction mixture, and the resulting layers were separated. The organic layer was washed with a 5% aqueous sodium hydrogencarbonate solution (12.9 L), a 5% aqueous potassium carbonate solution (12.9 L), 1N hydrochloric acid (12.9 L), water (12.9 L), and saturated saline (12.9 L) successively, and dried over anhydrous magnesium sulfate. The magnesium sulfate was separated by filtration and washed with tetrahydrofuran (18 L). The organic layer was concentrated to obtain the compound of the invention (3.61 kg; yield: 98%) having the following physical properties.

TLC: Rf 0.33 (hexane:ethyl acetate=1:1)

NMR (CDCl$_3$): δ8.78 (s, 1H), 7.60–7.30 (m, 10H), 6.74 (d, J=8.5 Hz, 1H), 5.43 (dd, J=8.5, 5.2 Hz, 1H), 5.23 (s, 2H), 4.64 (d, J=15.3 Hz, 1H), 4.60 (d, J=15.3 Hz, 1H), 2.50 (m, 1H), 1.47 (s, 9H), 1.06 (d, J=6.8 Hz, 3H), 0.87 (d, J=6.8 Hz, 3H).

EXAMPLE 4

Synthesis of N-((1RS)-1-(2-t-butyl-1,3,4-oxadiazol-5-ylcarbonyl)-2-methylpropyl)-2-(5-amino-6-oxo-2-phenyl-1,6-dihydropyrimidin-1-yl)acetamide

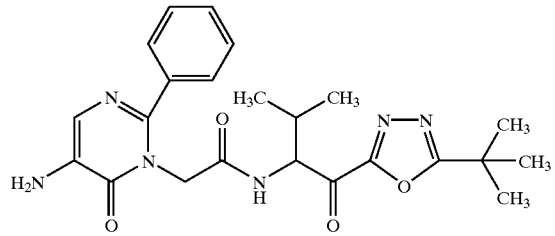

To a solution of the compound produced in Example 3 (1.61 kg) in methanol (27 L) was added 10% palladium-carbon (water content: 50%; 274 g) at room temperature in an argon atmosphere. Argon substitution was carried out three times, and then hydrogen substitution was carried out three times. The reaction mixture was stirred at 25° C. and 3 atm for 25 minutes. After argon substitution was carried out three times, the reaction mixture was filtered, and the filtrate was concentrated. The residue was dissolved in methanol (54.8 L), followed by filtration. Water (54.8 L) was added to the filtrate, and seed crystals (12.4 g) were added to thereto, followed by stirring overnight and then stirring at 5–100° C. for 1 hour. The precipitated crystals were collected by filtration, washed with water (30 L), and dried in vacuo at 60° C. for at least 38 hours to obtain the compound of the invention (1.90 kg; yield: 77%) having the following physical properties.

TLC: Rf 0.45 (methylene chloride:ethyl acetate:ethanol=10:10:1)

NMR (CDCl$_3$): δ7.58–7.35 (m, 6H), 6.94 (d, J=8.4 Hz, 1H), 5.44 (dd, J=8.4, 4.9 Hz, 1H), 4.66 (d, J=15.4 Hz, 1H), 4.60 (d, J=15.4 Hz, 1H), 4.06 (brs, 2H), 2.51 (m, 1H), 1.48 (s, 9H), 1.07 (d, J=6.9 Hz, 3H), 0.87 (d, J=6.9 Hz, 1H)

Comparative Examples

Among the compounds represented by formula (W-c-1), a compound in which $R^{1w}$ is a t-butyl group was produced by the processes shown in the previously described reaction schemes 2 and 3.

Comparative Example 1

Synthesis of t-butyl N-(1-formyl-2-methylpropyl)carbamate

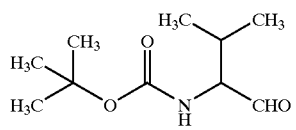

Diisobutylaluminum hydride (1.0 M toluene solution, 80 ml) was added dropwise to a solution of the compound produced in Reference Example 1 (9.0 g) in anhydrous tetrahydrofuran (500 ml) at −78° C. in an argon stream, followed by stirring for 30 minutes. Methanol (100 ml) was added to the reaction mixture, the temperature was raised to 0° C., and a saturated aqueous ammonium chloride solution (100 ml) was added thereto. The reaction mixture was filtered, and the filtrate was concentrated. The residue was purified by silica gel column chromatography (hexane:ethyl acetate=19:1→4:1) to obtain the title compound (5.4 g; yield: 78%) having the following physical properties.

TLC: Rf 0.55 (hexane:ethyl acetate=4:1)

NMR (CDCl₃): δ9.62 (s, 1H), 5.16 (brs, 1H), 4.25 (brs, 1H), 2.27 (m, 1H), 1.43 (s, 9H), 1.03 (d, J=6.6 Hz, 3H), 0.96 (d, J=6.6 Hz, 3H)

Comparative Example 2

Synthesis of t-butyl N-(1-(2-t-butyl-1,3,4-oxadiazol-5-yl)hydroxymethyl)-2-methylpropyl)carbamate

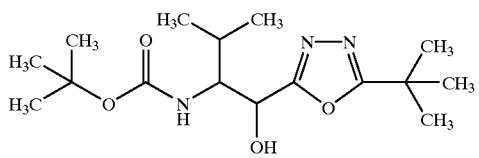

n-Butyl lithium (1.6 M hexane solution, 308 ml) was added dropwise to a solution of the compound produced in Reference Example 3 (62.1 g) in tetrahydrofuran (1.65 L) at −70° C. in an argon atmosphere, followed by stirring for 40 minutes. Magnesium bromide diethyl etherate (127 g) was added to the reaction mixture, and the temperature was raised to −45° C., followed by stirring for 1.5 hours. A solution of the compound prepared in Comparative Example 1 (90.0 g) in tetrahydrofuran (60 ml) was added to the reaction mixture, and the temperature was raised to −20° C., followed by stirring for 3.5 hours. A saturated aqueous solution of ammonia chloride (1.5 L) was added to the reaction mixture, followed by extraction with ethyl acetate (1.8 L). The organic layer was washed with water (1 L, three times) and saturated saline (1 L) successively, dried over anhydrous sodium sulfate, and concentrated. The residue was purified by silica gel column chromatography (ethyl acetate:hexane=1:20→1:1) to obtain the title compound (76.8 g; yield: 53%) having the following physical properties.

TLC: Rf 0.42 (ethyl acetate:hexane=1:1).

NMR (CDCl₃): δ5.18–4.90 (m, 2H), 4.51 and 4.12 (each m, totally 1H), 3.91 and 3.66 (each m, totally 1H), 1.95 (m, 1H), 1.42, 1.41 and 1.34 (each s, totally 18H), 1.15–0.90 (m, 6H).

Comparative Example 3

Synthesis of 1-(2-t-butyl-1,3,4-oxadiazol-5-yl) hydroxymethyl-2-methylpropylamine hydrochloride

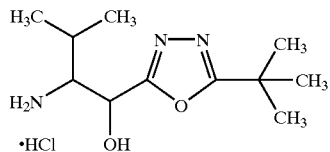

A solution of the compound produced in Comparative Example 2 (76.3 g) and a 4N hydrogen chloride-dioxane solution (1 L) in dioxane (200 ml) was vigorously stirred at room temperature for 2 hours, followed by concentration. The residue was solidified with diethyl ether and subjected to azeotropy with benzene to quantitatively obtain the title compound (66.1 g) having the following physical properties.

TLC: Rf 0.30 and 0.26 (methanol:chloroform=1:10)

NMR (CDCl₃): δ8.34 and 8.24 (each br, each 1H), 5.60 (br, 1H), 3.97–3.60 (m, 2H), 2.08 (m, 1H), 1.42 and 1.41 (each s, totally 9H), 1.25–0.95 (m, 6H).

Comparative Example 4

Synthesis of N-(1-(2-t-butyl-1,3,4-oxadiazol-5-yl) hydroxymetyl-2-methylpropyl)-2-(5-benzyloxycarbonylamino-6-oxo-2-phenyl-1,6-dihydropyrimidin-1-yl)acetamide

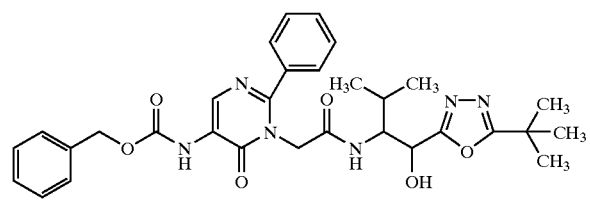

To a solution of the compound produced in Reference Example 9 (10.0 g) and the compound produced in Comparative Example 3 (8.16 g) in anhydrous dimethylformamide (88 ml) were added 1-hydroxybenzotriazole monohydrate (4.44 g) and 1-ethyl-3-(3-dimethylaminopropyl) carbodiimide hydrochloride (6.62 g) in an argon stream under cooling with ice, and N-methylmorpholine (3.19 ml) was added dropwise thereto. The reaction mixture was stirred under ice-cooling for 20 minutes and then at room temperature for 6.5 hours, followed by concentration. Ethyl acetate (100 ml) and water (100 ml) were added to the residue, and the resulting layers were separated. The organic layer was washed with a saturated aqueous solution of ammonium chloride (60 ml, twice), a saturated aqueous solution of sodium hydrogencarbonate (60 ml, twice), water (60 ml), and saturated saline (60 ml) successively, dried over anhydrous sodium sulfate, and concentrated. The resulting solid (14.7 g; yield: 95%) was used in the subsequent reaction without purification.

TLC: Rf 0.60 and 0.55 (chloroform:methanol=9:1)

NMR (CDCl₃): δ8.80 and 8.71 (each brs, total 1H), 7.64–7.24 (m, 11H), 7.15 and 6.79 (each brd, J=9.8 Hz, total 1H), 5.28–4.98 (m, ca. 1.5H), 5.20 (s, 2H), 4.69 (brs, ca. 0.5H), 4.58 and 4.46 (each brs, total 2H), 4.30 and 4.05 (each m, total 1H), 2.05–1.65 (m, 1H), 1.38 and 1.34 (each s, total 9H), 1.08, 0.96, 0.92, and 0.91 (each d, J=6.4 Hz, total 6H).

Comparative Example 5

Synthesis of N-(1-(2-t-butyl-1,3,4-oxadiazol-5-ylcarbonyl)-2-methylpropyl)-2-(5-benzyloxycarbonylamino-6-oxo-2-phenyl-1,6-dihydropyrimidin-1-yl)acetamide

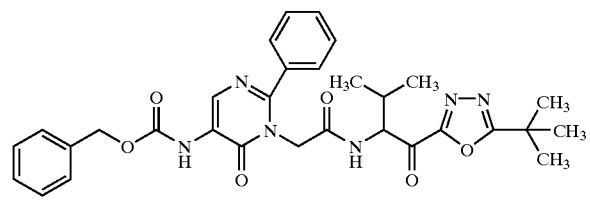

A solution of dimethyl sulfoxide (7.1 ml) in anhydrous methylene chloride (100 ml) was added dropwise to a solution of oxalyl chloride (4.4 ml) in anhydrous methylene chloride (100 ml) at −60° C. or lower in an argon stream, followed by stirring for 40 minutes. A solution of the compound produced in Comparative Example 4 (14.7 g) in a mixed solvent (anhydrous methylene chloride (75 ml) and dimethyl sulfoxide (10 ml)) was added dropwise to the reaction mixture at −60° C. or lower, followed by stirring for 2 hours. Triethylamine (69.8 ml) was added dropwise to the reaction mixture at −60° C. or lower, followed by stirring at room temperature overnight. The reaction mixture was cooled with ice, and 2N hydrochloric acid (200 ml) was added dropwise thereto. The organic layer was washed with 1N hydrochloric acid (150 ml), water (150 ml), and saturated saline (150 ml) successively, dried over anhydrous magnesium sulfate, and concentrated. The resulting solid (14.6 g; yield: 100%) was used in the subsequent reaction without purification.

Comparative Example 6

Synthesis of N-(1-(2-t-butyl-1,3,4-oxadiazol-5-ylcarbonyl)-2-methylpropyl)-2-(5-amino-6-oxo-2-phenyl-1,6-dihydropyrimidin-1-yl)acetamide

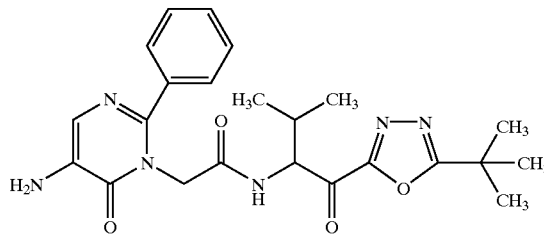

A solution of aluminum chloride (20.0 g) in nitromethane (70 ml) was added to a solution of the compound produced in Comparative Example 5 (14.4 g) and anisole (16.0 ml) in nitromethane (70 ml) under cooling with ice, followed by stirring under ice cooling for 10 minutes and then stirring at room temperature for 14 hours. The reaction mixture was poured into ice-water (200 ml) and extracted with ethyl acetate (120 ml and 40 ml). The organic layer was washed with a sodium chloride aqueous solution (a saturated sodium chloride aqueous solution (100 ml)+water (100 ml)) and saturated saline (200 ml) successively, dried over anhydrous magnesium sulfate, and concentrated. The residue was purified by silica gel column chromatography (hexane:ethyl acetate=1:2→0:1) to obtain a solid (6.7 g). The solid was washed with a mixed solvent (hexane:ethyl acetate=1:3) to obtain the title compound (5.2 g; yield: 46%).

What is claimed is:

1. A compound represented by formula (I):

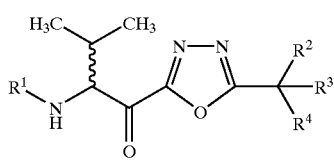

(I)

wherein

R$^1$ represents a hydrogen atom or an amino-protective group selected from the group consisting of methoxycarbonyl, ethoxycarbonyl, 9-fluorenylmethyloxycarbonyl, 2,2,2-trichloroethoxycarbonyl, 2-trimethylsilylethoxycarbonyl, 1,1-dimethylpropynyloxycarbonyl, 1-methyl-1-phenylethoxycarbonyl, 1-methyl-1-(4-biphenylyl)ethoxycarbonyl, 1,1-dimethyl-2-haloethoxycarbonyl, 1,1-dimethyl-2-cyanoethoxycarbonyl, t-butoxycarbonyl, cyclobutoxycarbonyl, 1-methylcyclobutoxycarbonyl, 1-adamantyloxycarbonyl, vinyloxycarbonyl, allyloxycarbonyl, cinnamyloxycarbonyl, 8-quinolyloxycarbonyl, N-hydroxypiperidinyl, benzyloxycarbonyl, p-nitrobenzyloxycarbonyl, 3,4-dimethoxy-6-nitrobenzyloxycarbonyl, 2,4-dichlorobenzyloxycarbonyl, 5-benzisoxazolylmethyloxycarbonyl, 9-anthrylmethyloxycarbonyl, diphenylmethyloxycarbonyl, isonicotinyloxycarbonyl, benzylthiocarbonyl, N'-phenylaminothiocarbonyl, formyl, acetyl, chloroacetyl, trichloroacetyl, trifluoroacetyl, benzoyl, allyl, phenylacetyl, methoxymethyl, benzyloxymethyl, 2,4-dinitrophenyl, 2-nitrobenzyl, 2-(trimethylsilyl)ethoxymethyl, benzyl, triphenylmethyl, p-toluenesulfonyl, benzenesulfonyl, and benzylsulfonyl;

R$^2$, R$^3$ and R$^4$ each independently represents
(1) a $C_{1-8}$ alkyl group,
(2) a $C_{3-7}$ cycloalkyl group,
(3) a phenyl group,
(4) a phenyl group substituted with one to three of a $C_{1-8}$ alkyl group, a $C_{1-8}$ alkoxy group, a halogen atom, a trifluoromethyl group, and a trifluoromethoxy group, or
(5) a 3,4-methylenedioxyphenyl group; or
(6) R$^3$ and R$^4$ are taken together to represent a $C_{2-6}$ alkylene group, a non-toxic salt thereof or a hydrate thereof.

2. The compound according to claim 1, wherein R$^1$ represents a hydrogen atom in formula (I), said compound being represented by formula (I-1):

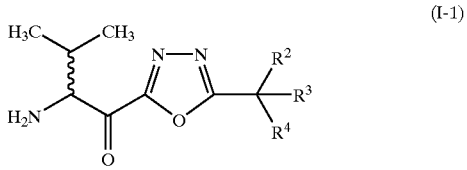

(I-1)

(wherein R$^2$, R$^3$ and R$^4$ have the same meanings as in claim 1).

3. The compound according to claim 1, wherein R$^1$ represents a benzyloxycarbonyl group, a t-butoxycarbonyl group or a trifluoroacetyl group in formula (I), said compound being represented by formula (I-2):

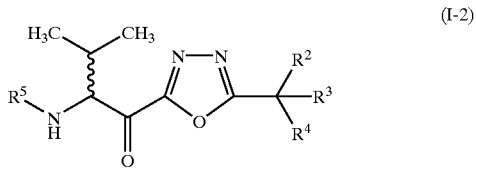

(I-2)

(wherein R$^5$ represents a benzyloxycarbonyl group, a t-butoxycarbonyl group or a trifluoroacetyl group; and R$^2$, R$^3$ and R$^4$ have the same meanings as in claim 1).

4. The compound according to claim 1, wherein R$^2$, R$^3$ and R$^4$ each independently represents a $C_{1-8}$ alkyl group, a phenyl group or a 3,4-methylenedioxyphenyl group, or R$^3$ and R$^4$ are taken together to represent a $C_{2-5}$ alkylene group in formula (I).

5. The compound according to claim 4, wherein $R^2$, $R^3$ and $R^4$ each represents a methyl group; $R^2$ represents a methyl group, and $R^3$ and $R^4$ are taken together to represent an ethylene group; $R^2$ and $R^3$ each represents a methyl group, and $R^4$ represents a phenyl group; or $R^2$ and $R^3$ each represents a methyl group, and $R^4$ represents a 3,4-methylenedioxyphenyl group.

6. The compound according to claim 2, which is (1) 1-(2-t-butyl-1,3,4-oxadiazol-5-ylcarbonyl)-2-methylpropylamine, or
(2) 1-(2-(α,α-dimethylbenzyl)-1,3,4-oxadiazol-5-ylcarbonyl)-2-methylpropylamine.

7. The compound according to claim 3, which is (1) t-butyl N-(1-(2-t-butyl-1,3,4-oxadiazol-5-ylcarbonyl)-2-methylpropyl)carbamate, or
(2) t-butyl N-(1-(2-(α,α-dimethylbenzyl)-1,3,4-oxadiazol-5-ylcarbonyl)-2-methylpropyl)carbamate.

8. A process for producing a compound represented by formula (I-2):

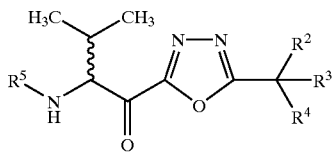

(I-2)

(wherein symbols in the formula have the same meanings as described below), comprising reacting a compound represented by formula (V):

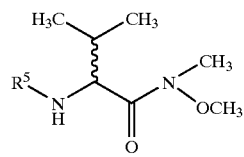

(V)

(wherein $R^5$ has the same meaning as in claim 3) with a compound represented by formula (VI):

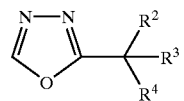

(VI)

(wherein $R^2$, $R^3$, and $R^4$ have the same meanings as in claim 1).

9. A process for producing a compound represented by formula (I-1):

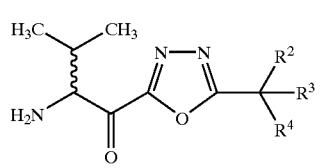

(I-1)

(wherein symbols in the formula have the same meanings as described below), comprising subjecting a compound represented by formula (I-2):

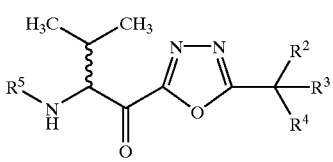

(I-2)

(wherein $R^2$, $R^3$, $R^4$ and $R^5$ have the same meanings as in claim 3) to a deprotection reaction of the amino-protecting group.

* * * * *